United States Patent [19]

Dake et al.

[11] 4,112,167
[45] Sep. 5, 1978

[54] SKIN CLEANSING PRODUCT HAVING LOW DENSITY WIPING ZONE TREATED WITH A LIPOPHILIC CLEANSING EMOLLIENT

[75] Inventors: Timothy William Dake; James Spence Clunie; Allen Dale Early, all of Cincinnati, Ohio

[73] Assignee: The Procter & Gamble Company, Cincinnati, Ohio

[21] Appl. No.: 757,712

[22] Filed: Jan. 7, 1977

[51] Int. Cl.² ............... B32B 3/00; B32B 21/04
[52] U.S. Cl. ............... 428/154; 428/153; 428/155; 428/156; 428/158; 428/159; 428/171; 428/289; 428/302; 428/304; 428/318; 428/537
[58] Field of Search ............... 428/131, 537, 134–138, 428/152–155, 170–173, 212, 213, 218, 302, 304, 305, 323, 327, 913, 289; 424/27, 28, 172; 162/113, 123, 132

[56] References Cited

U.S. PATENT DOCUMENTS

| | | | |
|---|---|---|---|
| 2,902,395 | 9/1959 | Hirschy et al. | 428/302 |
| 2,999,265 | 9/1961 | Duane et al. | 424/28 X |
| 3,150,049 | 9/1964 | Emory | 424/28 |
| 3,310,454 | 3/1967 | Florio et al. | 428/171 X |
| 3,366,532 | 1/1968 | Maskey et al. | 428/318 X |
| 3,595,731 | 7/1971 | Davies et al. | 428/151 |
| 3,708,435 | 1/1973 | Starkman | 424/168 X |
| 3,759,775 | 9/1973 | Shepherd | 428/170 X |
| 3,818,105 | 6/1974 | Coopersmith et al. | 428/168 X |
| 3,823,057 | 7/1974 | Roberts et al. | 428/137 X |
| 3,829,563 | 8/1974 | Barry et al. | 428/168 X |
| 3,881,210 | 5/1975 | Drach et al. | 428/154 X |
| 3,896,807 | 7/1975 | Buchalter | 428/28 X |
| 3,949,130 | 4/1976 | Sabee et al. | 428/192 |
| 3,993,820 | 11/1976 | Repke | 428/171 X |
| 3,994,771 | 11/1976 | Morgan et al. | 428/180 X |

*Primary Examiner*—Lorraine T. Kendell
*Attorney, Agent, or Firm*—John M. Pollaro; Fredrick H. Braun; Richard C. Witte

[57] ABSTRACT

An article of manufacture is disclosed for cleansing the skin with improved effectiveness. A soft, flexible web having a low density wiping zone works in concert with a lipophilic cleansing emollient to remove soil from the skin with improved effectiveness. The lipophilic cleansing emollient reduces dehydration of the soil and weakens the soil-skin adhesive forces while the low density wiping zone of the web entraps and thus removes the soil from the skin.

15 Claims, 3 Drawing Figures

SKIN CLEANSING PRODUCT HAVING LOW DENSITY WIPING ZONE TREATED WITH A LIPOPHILIC CLEANSING EMOLLIENT

BACKGROUND OF THE INVENTION

This invention generally relates to soft, pliant skin cleansing products. More particularly, this invention relates to soft, pliant skin cleansing products which have a low density wiping zone and which are treated with a lipophilic cleansing emollient. Still more particularly, this invention relates to soft, pliant anal cleansing webs, generally referred to as toilet tissue, which are treated with a lipophilic cleansing emollient.

Cleansing the skin is a personal hygiene problem not always easily solved. Of course, the common procedure of washing the skin with soap and water works well, but at times soap and water may be either unavailable or inconvenient to use. While soap and water could be used to clean the perianal region after defecation for example, such a procedure would be extremely burdensome and therefore dry tissue products are the most commonly used post-defecation anal cleansing product.

The perianal skin is marked by the presence of fine folds and wrinkles (sulci) and by hair follicles, both of which serve to make the perianal region one of the more difficult anatomical areas to cleanse. During defecation, fecal matter is excreted through the anus and tends to accumulate in hard to reach locations such as around the base of hairs and in the sulci of the skin's surface. As the fecal matter dehydrates upon exposure to the air, or upon contact with an absorbent cleansing implement such as tissue paper, it adheres more tenaciously to the skin and hair, thus making subsequent removal of the remaining dehydrated soil even more difficult.

Failure to remove fecal matter from the anal area can have a deleterious effect on personal hygiene. The fecal matter remaining on the skin after post-defecation cleansing has a high bacterial and viral content, is malodorous and is generally dehydrated. These characteristics increase the likelihood of perianal disorders and cause personal discomfort (e.g. itching, irritation, chafing, etc.). Further, the residual fecal matter stains undergarments and causes unpleasant odors to emanate from the anal region. Thus, the consequences of inadequate perianal cleansing are clearly unattractive.

For those individuals suffering from anal disorders such as pruritis ani, hemorrhoids, fissures, cryptitis, or the like, the importance of adequate perianal cleansing takes on heightened significance. Perianal disorders are usually characterized by openings in the skin through which the bacteria and viruses in the residual fecal matter can readily enter. Those people afflicted with anal disorders must, therefore, achieve a high degree of perianal cleansing after defecation or risk the likely result that their disorders will be aggravated by the bacteria and viruses remaining on the skin.

At the same time anal disorder sufferers face more severe consequences from insufficient post defecation cleaning, they face a greater difficulty in achieving a satisfactory level of soil removal. Anal disorders generally render the perianal region extremely sensitive and attempts to remove fecal matter from this region by wiping with even normal wiping pressure causes pain and may further irritate the skin. Attempts to increase soil removal by increasing the wiping pressure results in intense pain, while attempts to reduce the discomfort associated with wiping by reducing the wiping pressure results in an increase in the amount of residual fecal matter left on the skin. When using prior art anal cleansing products, the sufferer of anal disorders is thus faced with the Scylla of inadequate post defecation cleaning and the Charybdis of increased wiping pressure.

The prior art products used for anal cleaning are essentially dry, high density tissue paper products which rely exclusively on mechanical processes to remove fecal matter from the perianal skin and are hereinafter referred to as conventional products. Thus, the conventional product is rubbed against the perianal skin, typically with a pressure of about 1 pound per square inch (psi) (7 kilopascals) and basically scrapes or abrades the fecal matter from the skin. On the first few wipes, the upper portion of the soil layer is removed because the wiping process is able to overcome the soil-soil cohesive forces that exist within the fecal matter. A cleavage is thereby created in the soil layer itself with the upper portion of the fecal layer being removed and the lower portion of the soil remaining adhered to the perianal skin.

Conventional tissue products are absorbent and with each successive wipe the fecal matter becomes increasingly dehydrated, causing the fecal matter to adhere more tenaciously to the perianal skin and hair thereby making its removal difficult in the extreme. Pressing the tissue forcefully against the perianal skin will remove more of the fecal matter but, as discussed hereinbefore, this alternative is intensely painful for people suffering from anal disorders and can excoriate even normal perianal skin possibly causing irritation, inflammation, pain, bleeding, and infection.

To reduce the abrasive effect of the tissue and to increase its softness impression conventional tissue is generally manufactured having smooth wiping surfaces (i.e. little surface contour or texture). To further improve the comfort and cleaning performance of conventional toilet tissues, the prior art teaches treating such tissues with various additives. Of course, a wide variety of treated paper products, both for anal cleaning and for multifarious other uses, have long been known and many such products are currently being marketed.

The prior art teachings seek to improve the characteristics of conventional products by merely treating the paper with an additive. For example, U.S. Pat. Nos. 302,073 and 2,833,669 to Wheeler and Mainz, respectively, teach the concept of applying an antiseptic or disinfectant to a paper web. Additionally, U.S. Pat. Nos. 1,687,625 and 3,264,188 to Mackenzie and Gresham, respectively, teach treating the paper web with an organic chemical additive to improve the comfort and cleaning ability of the web. Likewise, German Offenlegungsschrift publication No. 2,260,612 to Scheffler and U.S. Pat. Nos. 3,619,280 to Scheuer and Re 29,052 to Bucalo, disclose a toilet tissue treated with an additive to enhance a variety of characteristics of the paper such as cleaning and softness. Finally, Canadian Pat. No. 977,197 to Schapira teaches a sanitary paper treated with a variety of substances such as deodorants, epidermal emollients and bactericides.

The prior art products, particularly those used for anal cleaning, are high density tissue paper products which have a small void volume in the wiping zone and treatment of these products with the various additives suggested in the prior art can improve some of the product's characteristics (e.g., softness, antibacterial properties, etc.) depending upon the additive used. If only the cleansing properties of the tissue papers are considered, however, the addition of an additive may or may not improve the cleansing ability of the paper. For conventional prior art tissue papers the addition of some additives may actually reduce the cleansing ability of the paper.

The prior art skin cleansing products lack the aspects of the present invention whereby improved skin cleansing effectiveness is obtained by treating a web having a low density (i.e., high void volume) wiping zone with a lipophilic cleansing emollient. The present invention thus exhibits improved cleansing effectiveness when compared to prior art products and also exhibits an unexpected cleaning improvement when compared to the corresponding untreated low density web.

It is therefore an object of the present invention to provide a skin cleansing product having improved skin cleansing properties.

A further object of the present invention is to provide a product having a low density wiping zone which acts in concert with lipophilic cleansing emollients to cleanse the skin.

An additional object of the present invention is to provide a product having a high void volume in the wiping zone which acts in concert with lipophilic cleansing emollients to cleanse the skin.

These and other objects of the invention will be more readily apparent when considered in reference to the following description and when taken in connection with the accompanying drawings.

SUMMARY OF THE INVENTION

According to the present invention, a skin cleansing product is manufactured such that the wiping zone has a low density and is soil permeable under normal wiping pressures of about 1 psi (7 kilopascals). A low density wiping zone is characterized by a high void volume as indicated by the average void index. The average void index takes into account both surface voids (i.e., those voids formed by depressions in the surface of the web thus contributing to the surface contours and texture) and subsurface voids (i.e., those voids below the surface of the web).

The low density wiping zone of the web is treated with a lipophilic cleansing emollient which acts in concert with the low density wiping zone to provide an unexpected increase in the amount of soil removed from the skin. This unexpected increase in the cleansing effectiveness of the present invention results from the synergistic interaction between the lower density wiping zone and the lipophilic cleansing emollient.

As the wiping zone is rubbed over the skin, the lipophilic cleasing emollient is transferred to and coats both the soil and the skin. During the wiping process large amounts of soil become entrapped in the openings and pores of the low density wiping zone due to the interaction of the lipophilic cleansing emollient and the low density wiping zone and because the wiping zone is soil permeable, the soil is able to penetrate and become entrapped throughout the wiping zone. The transferred lipophilic cleansing emollient reduces dehydration of the soil layer and weakens the soil-skin adhesive forces thereby permitting larger amounts of soil to be removed on continued wiping.

DESCRIPTION OF THE PREFERRED EMBODIMENT

Referring now to the figures, there is shown a preferred embodiment of the present invention as it would be used in a skin cleansing product that is especially suited to cleansing the anal area. It should be understood, however, that the present invention is broadly applicable to the art of skin cleansing devices and that the following description of an anal cleansing product is merely intended to illustrate a preferred embodiment of the present invention.

Figure 1:
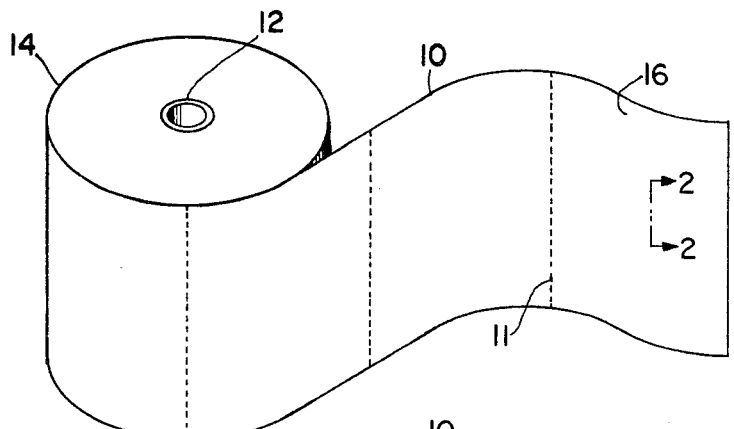
FIG. 1 is a perspective view of the present invention in roll form as an anal cleansing product.

As best seen in FIG. 1, the preferred embodiment basically comprises a web 10 suitable for use in anal cleansing. As used herein, the term web refers to a soft, pliant sheet or sheet-like structure. Most preferably, web 10 is manufactured from natural and/or synthetic fibers as are used and well known in the web making art generally, and in the papermaking art particularly, and includes structures which contain one or more plies of unitary papers or one or more plies of layered papers, or a combination thereof. Unitary papers are those papers which are discrete sheets of typically homogeneous santiary tissue which may, for example, be of the type described in U.S. Pat. No. 3,301,746 to Sanford et al. Layered papers are those papers which also are discrete sheets, but which have two or more layers bonded together by papermaking fiber bonds and may be, for example, of the type described in U.S. Pat. No. 3,994,771 to Morgan et al. Multiply structures are those structures formed by bonding together two or more discrete sheets of unitary papers, layered papers, or a combination thereof such as by glueing or embossing.

Web 10 may be provided in roll form, as is commonly done with commercial prior art products, by winding web 10 around core 12 to form roll 14 which is approximately 4.5 to 5.0 inches (11.5 to 12.5 centimeters) in diameter. The height of roll 14 is also approximately 4.5 inches (11.5 centimeters) which is typical of commonly marketed products and is therefore preferred. Other diameters and heights or even other dispensing systems, however, may be used. It is not necessary, however, that web 10 be contained in any special container when in use. Further, web 10 preferably has perforated lines 11 at conveniently spaced intervals to facilitate tearing of web 10.

Web 10 is preferably manufactured from fibrous materials which are readily disposable. As used herein, disposable refers to webs 10 which are intended for a single use before being discarded and which may be introduced into sewage disposal systems without deleterious effects either to home plumbing systems or to municipal or home waste treatment facilities. Further, web 10 is soft and pliant to prevent substantial abrasion of the anal area under normal wiping pressure and to permit web 10 to conform to the contours of the area being cleansed.

Figure 2:
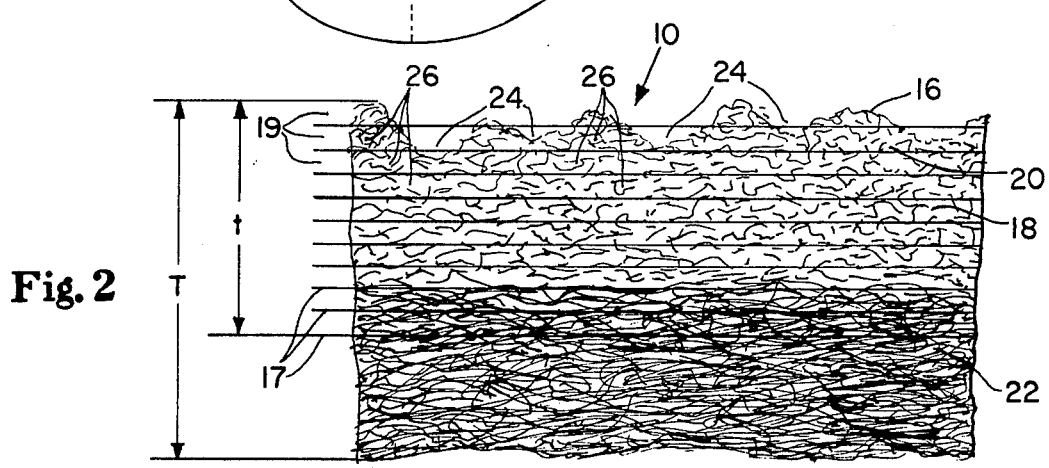
FIG. 2 is a greatly enlarged fragmentary edge view of the present invention under a load of 1 psi (7 kilopascals) taken along Section 2—2 in FIG. 1.

Referring now to FIG. 2, it can be seen that web 10 has at least one wiping surface 16 which forms the outer boundary of wiping zone 18. Web 10 is shown in FIG. 2 under 1 psi (7 kilopascals) pressure to illustrate the papers configuration under normal wiping pressure. Wiping zone 18 has a thickness "t" extending inwardly from wiping surface 16 for a distance of 150 microns (150 micrometers). For webs 10 having a caliper "T" less than 150 microns (150 micrometers) the wiping zone 18 will have a thickness "t" equal to the caliper "T" of the web 10. Wiping surface 16 is the surface of web 10 which is rubbed against the skin during the cleansing operation.

Wiping zone 18 is defined to be a maximum of 150 microns (150 micrometers) thick because for webs 10 having a caliper "T" greater than 150 microns (150 micrometers) the vast majority of the soil is entrapped in the first 150 microns (150 micrometers) of web 10. For webs 10 having a caliper "T" less than 150 microns (150 micrometers), the soil may penetrate the entire thickness of web 10.

Web 10 may be manufactured using any of the well-known web making processes which will cause web 10 to have a low density wiping zone 18 (as defined hereinafter) under normal wiping pressures. The preferred web 10 is a single ply of a layered paper construction, as shown in FIG. 2, having a first layer 20 and a second layer 22. U.S. Pat. No. 3,994,771 to Morgan et al., which is incorporated herein by reference, describes with admirable clarity a layering process by which such a layered web 10 is manufactured.

While not wishing to describe the Morgan et al. layering process in detail, a summary of that process is necessary for a better understanding of the present preferred embodiment. It should be noted that the Morgan et al. process may be practiced otherwise than as described hereinafter and that the description infra is merely one method of utilizing the Morgan et al. teachings. Accordingly, first layer 20 is formed from a first slurry of relatively short papermaking fibers (i.e., hardwood fibers) having a length of from about 0.01 inches (0.25mm) to about 0.06 inches (1.5mm). The slurry has a consistency of about 0.3 percent and is delivered from a headbox to a first fine mesh Fourdrinier wire. Most preferrably, the first layer 20 is formed from Eucalyptus fibers, although a wide range of other hardwood fibers may be used.

Second layer 22 is formed on a second fine mesh Fourdrinier wire from a second slurry comprising from about 50 to 100 percent relatively long papermaking fibers (i.e., softwood fibers) having a length of from about 0.080 inches (2.0mm) to about 0.120 inches (3.0mm) and 0 to 50 percent relatively short hardwood fibers as described above. In manufacturing the preferred web, a second slurry composition of 70 percent long papermaking fibers and 30 percent short papermaking fibers having a consistency of about 0.3 percent was used to form second layer 22.

A first vacuum is used to transfer first layer 20 to the outermost surface of second layer 22 thereby forming layered web 10 and a second vacuum of from about 10 to about 25 inches of mercury is used to transfer layered web 10 to an imprinting/drying fabric. First layer 20 is in contact with the fabric and the individual fibers of first layer 20 are displaced through the openings of the fabric. The fabric used to manufacture the preferred web 10 is preferably of semi-twill weave which is treated in accordance with the teachings of U.S. Pat. No. 3,905,863 to Ayers which is incorporated herein by reference. The fabric preferably has between about 10 and about 25 filaments per inch (4 to 10 filaments per cm) in both the woof and warp directions and has a diagonal free span across the fabric openings of from about 0.030 to about 0.060 inches (0.76 to 1.52mms).

Web 10 is thermally predried to a consistency of from about 65 to about 95 percent without disturbing its relationship to the fabric before being transferred to a Yankee dryer for final drying. The dried web 10 has a basis weight of from 15 to 45 pounds per 3,000 square feet (24 to 73 gms per square meter) with each layer having a basis weight of from 8 to 25 pounds per 3,000 square feet (13 to 41 gms per square meter). Web 10 is creped from the Yankee dryer with a doctor blade so that between 15 and 30 percent crepe is obtained. In the preferred embodiment, a basis weight of 30 pounds per 3,000 square feet (49 gms per square meter) was used with a crepe of 25 percent. The basis weight of each layer is 15 pounds per 3,000 square feet (24 gms per square meter).

Calendering is kept to a minimum and is preferably omitted. Wet and dry strength additives may be used to provide a tensile strength of from about 0.44 to 1.54 pounds per inch (78 to 275 gms per cm) in both the machine and cross-machine directions. For example, wet strength additives such as polyacrylamide as, for example, marketed under the tradename Parez 631NC by American Cyanamid Company of Wayne, New Jersey, and dry strength additives such as polyacrylamide polymer with a tertiary amine functional group as manufactured by American Cyanamid Company and marketed under the tradename Accostrength 98, can be added to the pulp slurries in amounts varying from about 0 to 15 pounds per ton of fibers (0 to 8 grams per kilogram of fibers) to obtain the desired wet and dry strength properties. The high basis weight and tensile strength helps web 10 retain its low density when subjected to normal wiping pressures. In the preferred embodiment the caliper of web 10 is between 15 and 35 mils (0.38 and 0.8mm)when measured at a pressure of 0.176 pounds per square inch (1.21 kilopascals).

Other methods of producing web 10 may also be used. For example, air laid fibers may be used to manufacture webs 10 commonly referred to as non-woven products. Many suitable methods of manufacturing webs 10 having a low density in the wiping zone are known in the art of web making generally and papermaking particularly.

Still referring to FIG. 2, it can be seen that wiping zone 18 has both surface voids 24 and subsurface voids 26. Surface voids 24 are those voids which contribute to the contours or texture of wiping surface 16 and may be viewed as being depressions in wiping surface 16. Subsurface voids 26 on the other hand, are those voids below wiping surface 16.

In wiping zones 18 having a low density, the volume that is taken up by voids will be a high proportion of the total volume of wiping zone 18. The ratio of void volume to total volume for wiping zone 18 is approximated by the average void index which takes into account both surface voids 24 and subsurface voids 26 and which is determined in accordance with the procedure described hereinafter. Thus, a low density wiping zone 18 will have a high average void index.

To determine the average void index of web 10, a sample of web 10 is embedded with a suitable medium which will completely fill both the surface voids 24 and the subsurface voids 26. The embedding medium should be fluid enough to permeate web 10 completely, leaving no air bubbles in the voids and must harden with no significant dimensional changes when cured. In addition, the embedding medium must not be absorbable by the solid portions of web 10.

A preferred embedding medium which was found to work well is a mixture (percent by volume) of: 46 percent polyamid resin such as Versamid 125 as marketed by General Mills Chemical Inc., of Kankakee, Illinois; 31 percent epoxy resin such as EPON Resin 812 as marketed by Fisher Scientific of Fair Lawn, New Jersey; and 23 percent trichloroethane. Web 10 is immersed in the embedding medium and a 1 pound (454 gms) stainless steel weight having a one square inch (6.45 square cms) cross sectional area is placed on web 10 and the embedding medium is cured. The preferred embedding medium given above is cured (i.e., polymerized) after standing at 70° F. (21° C.) for 16 hours. The one pound (454 gm) weight will compress 1 square inch (6.45 square cms) of web 10 and cause the excess embedding medium to flow out of web 10 before curing thereby forming a flared portion which may be trimmed after web 10 is cured.

Wiping zone 18 of the embedded web 10 is microtomed using a microtome such as Model 860 as marketed by American Optical Company of Buffalo, New York. By the process of microtoming the wiping zone 18 is cut along lines 17 in a direction generally perpendicular to the web thickness "T" forming serial sections 19 each 15 microns (15 micrometers) thick starting from the top of wiping surface 16. If the thickness "T" of web 10 is less than 150 microns (150 micrometers) the entire web is cut into as many serial sections 19 that are 15 microns (15 micrometers) thick as possible while webs 10 that are 150 microns (150 micrometers) or greater are cut into a maximum of 10 serial sections 19 each 15 microns (15 micrometers) thick. The microtoming process described above is followed for all webs 10 irrespective of whether they are unitary or layered, multi-ply or single ply structures.

The serial sections are mounted on a glass microscope slide in conventional fashion using an immersion oil with a refractive index indentical to the web embedding medium but different from the soild portions of web 10 and photomicrographed. For use with the paper fibers described supra an immersion oil having a refractive index of 1.515 was found to work satisfactorily. A suitable microscope is Model 18 as manufactured by Carl Zeiss of Oberkochen, West Germany which is marketed and used with a blue filter and a neutral optical density filter. Polarized light is transmitted through the mounted serial section and a photomicrograph taken at a magnification of 32. A camera which was found to work well was Model MP4 as manufactured by Polaroid Corporation of Cambridge, Massachusetts. Polaroid type 55 film and a 1 second exposure time were likewise found to result in satisfactory photomicrographs.

From the photomicrograph of each serial section the corresponding void index can be determined. The void index of each serial section is the percentage of web 10 that is the portion of the photomicrograph area which depicts void portions of web 10 and may be determined using any appropriate method. It has been found that stochastic methods, such as a Monte Carlo technique, work well. Accordingly, a series of random points or dots is generated and plotted on a transparent sheet which covers at least 4 square inches (26 sq. cm) of the photomicrograph being analyzed. A suitable sheet having random dots already plotted is the Bruning Areagraph Chart 4850 manufactured by Bruning Division of Addressograph Multigraph Corporation of Cleveland, Ohio.

The transparent sheet is laid over the photomicrograph of a serial section and the number of void points, (i.e. those dots having at least one half of their total area covering a void portion of the serial section) are counted. The ratio of void points to the total number of random points within the area of the photomicrograph when expressed as a percentage is the void index of the serial section under investigation.

The average void index is the average of the void indices for the individual serial sections taken in wiping zone 18. For webs 10 having a thickness "T" at least 150 microns (150 micrometers), the average void index will be the average of the void indices for the first 10 serial sections. For webs 10 less than 150 microns (150 micrometers) thick, the average void index will be the average of the void indices for all the serial sections that can be cut from web 10. The minimum void index is the lowest of the void indices used to determine the average void index.

Serial sections 19 having a maximum thickness of 15 microns (15 micrometers) are used to minimize the error inherent in measuring volumes from two dimensional photographs. If thick serial sections 19 were used, large portions of the void volume could be obscured and this could contribute to a significant error causing the average void index not to be indicative of the void volume of web 10.

Low density wiping zones 18 will have a high average void index. As used herein, a high average void index is at least 68. Thus, low density wiping zones are those having an average void index which are at least 68 and high density wiping zones are those having an average void index less than 68. It must be emphasized, however, that the average void index is determined for webs 10 which are subjected to a uniform pressure of 1 psi (7 kilopascals). The average void index for uncompressed webs 10 is not significant.

While webs 10 having an average void index of at least 68 are preferred, webs 10 having an average void index of at least 70 are more preferred and webs 10 having a void index of at least 75 are most preferred.

To effectively clean, the wiping zone 18 must also be permeable to soil. To ensure the required permeability, the wiping zone 18 must not have a soil impermeable layer. Therefore, the minimum void index for any serial section within the wiping zone must be greater than about 10. If the minimum void index of a serial section is less than about 10, that section may act as an impermeable barrier preventing the soil from reaching all portions of wiping zone 18.

The error associated with the hereinbefore describe Monte Carlo method of measuring void indices of serial sections 19 is determined by the following equation:

$$E = \pm 1.96 \sqrt{V(100 - V)/n}$$

where:
$E$ = the error associated with the measurement
$V$ = void index of an individual serial section 19
$N$ = number of random points used to determine V.

From this, it follows that increasing the number of random points increases the accuracy of the void index measurements. It has been found that 400 random points in a 4 square inch (26 sq. cm) area will give a measurement error that is less than ± 5 and that larger errors are unsatisfactory. The effects of variations between paper samples can be minimized by increasing the number of samples subjected to the foregoing procedures.

The use of three samples randomly taken from the paper whose void index is to be determined has been found to be sufficient to minimize the variations in characteristics inherent in paper products.

The cleaning effectiveness of web 10 is determined from tests involving fecally soiled pig skins conducted in the following manner. Fecal matter is collected from several donors, blended together, freeze dried, and sterilized with ethylene oxide to kill the bacteria and deactivate the viruses normally present in the fecal sample. Before use in cleaning tests, the fecal matter is reconstituted with distilled water to 25 percent by weight of solids, loaded into a syringe and placed under a heat lamp to maintain the fecal matter at a temperature of 92° F. (34° C.).

The skin from the back of a white pig has a superficial resemblance to human skin, containing fine intersecting lines (sulci) which form characteristic geometric patterns. In addition, swine skin has wetting properties and hair characteristics similar to those of human skin and for these reasons swine skin is used in cleaning tests to simulate human skin.

Figure 3:
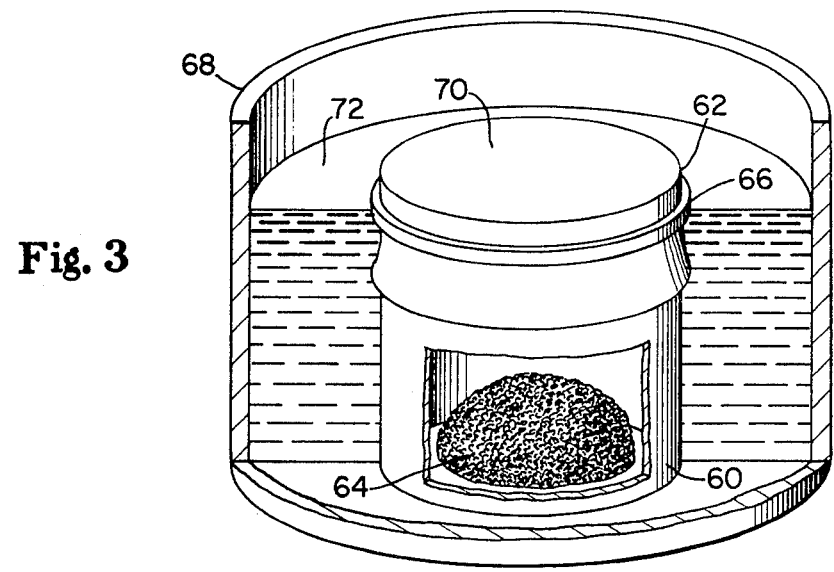
FIG. 3 is a partially cut away sectional view of the apparatus used for the cleaning tests.

Referring to FIG. 3, the layer of fat on the dermal side of the swine skin is removed and the skin 62 secured to a stainless steel container 60 having a diameter of 2 inches (5 cm) and a height of 0.5 inches (1.25 cm) in which a sponge 64 saturated with a 0.9% saline solution is place to prevent the skin from drying during testing. An elastic band 66 may be used to hold swine skin 62 in place and seals the dermal side of swine skin 62 from the environment. The hair on the swine skin is trimmed to a length of about ¼ to ½ inch. (0.62 to 1.25 cms) and the container placed in a water bath 68 containing a saturated potassium acetate solution at 100° F. (38° C.), with the skin surface 70 lying above water surface 72, and allowed to equilibrate for approximately 30 minutes. Ambient conditions are 73° F. (23° C.) and 50% relative humidity. These conditions maintain the swine skin at a temperature of 90° F. (32° C.) and a humidity at the skin surface equal to the ambient humidity.

The swine skin is removed from the water bath and 200 milligrams (50 milligrams of solids) of reconstituted fecal matter is spread evenly over a 5 square centimeter area. The swine skin is then placed on a scale platform and wiped with the anal cleaning product to be tested in a direction perpendicular to the grain of the hair using a 1,000 gram force normal to the skin surface as measured by the scale.

After eight wipes (each wipe with a fresh piece of tissue), the skin is compared to a graded series of 11 photographs and the amount of soil remaining on the test skin determined by visual comparison with the photographs. The photographs show a swine skin soiled with various amounts of fecal matter ranging from clean (0 milligrams of solids/10 sq. cm.) to heavily soiled (27.5 milligrams of solids/10 sq. cm.). The soil remaining on the wiped swine skin is determined by interpolation from the photographs of the soiled skins that most closely resemble the test skin. The cleaning effectiveness of web 10 is thus determined by the amount of soil remaining on the test skin after 8 wipes. The lower the weight of soil remaining on the test skin after 8 wipes, the more effective is the skin cleaning product.

The cleansing effectiveness of web 10 having a high average void index is unexpectedly enhanced by treating web 10 with a lipophilic cleansing emollient. As used herein, the term lipophilic cleansing emollient refers to an essentially non-polar, nonaqueous, oil-based composition which when applied to the surface of the skin forms a thin film. The lipophilic cleansing emollient may or may not penetrate the epidermis and is nonvolatile, nontoxic, nonhygroscopic, and is well-tolerated by skin.

In general, lipophilic cleansing emollients are compounds or mixtures of compounds which are mainly paraffinic hydrocarbons and their common derivatives (e.g., fatty alcohols, acids and esters) which when applied to the skin, spread over the skin's surface because of their low surface tension against air (less than about 35 dynes per cm at 25° C.). Further, lipophilic cleansing emollients have a rheology typical of pseudoplastic or plastic fluids. When no shear is applied lipophilic cleansing emollients have the appearance of a semi-solid but can be made to flow as the shear rate is increased. Still further, these lipophilic cleansing emollients exhibit decreasing viscosity with increasing shear rate. The lipophilic cleansing emollient should have a viscosity no greater than 5,000 cps. when measured at a shear rate of 400 sec $^{-1}$ at a temperature of 25° C. Included within this definition are silicone oils and waxes which, although non-paraffinic in origin, satisfy the above specified physical criteria.

Lipophilic cleansing emollients, as hereinbefore defined, are commonly used as oil-based skin cleansers in the cosmetic art. Specific examples of individual substances included in the term "lipophilic cleansing emollients" are: paraffinic hydrocarbons (straight or branched chain, saturated or unsaturated), having chain lengths of from 16 to 60 carbon atoms, such as mineral oil ($C_{16}$ to $C_{20}$) petrolatum ($C_{16}$ to $C_{32}$), paraffin waxes ($C_{20}$ to $C_{40}$) and micro-crystalline waxes ($C_{35}$ to $C_{60}$); alkyl esters derived from monocarboxylic fatty acids having from 12 to 28 carbon atoms and short chain ($C_2$ to $C_8$) monohydric alchols, such as isopropyl laurate, isopropyl myristate, isopropyl palmitate, ethyl hexyl palmitate; alkyl esters derived from fatty alchols ($C_{12}$ to $C_{28}$) and short chain acids e.g., lactic acid, such lauryl lactate, cetyl lactate; fatty acids, fatty alcohols and fatty alcohol ethers having from 12 to 28 carbon atoms in their fatty chain, such as stearic acid, cetyl alcohol, ethoxylated and propoxylated fatty alcohols; glycerides, acetoglycerides, and ethoxylated glycerides of $C_{12}$ to $C_{28}$ fatty acids; other fatty esters of polyhydroxy alcohols; lanolin and its derivatives; polysiloxanes having a viscosity at 25° of from 5 to about 2,000 centistokes and having the formula—$[R_1R_2SiO_2]_n$— wherein R is $C_1$ to $C_4$ alkyl or phenyl.

The term lipophilic cleansing emollient also includes mixtures of these individual substances in all proportions and in all combinations. It is desirable, however, that the lipophilic cleansing emollient not be self-dripping after application to web 10 at the prescribed levels.

Web 10 may be treated with the lipophilic cleansing emollient by any suitable method such as by spraying. As used herein, the term "treating" also encompasses such methods of applying the lipophilic cleansing emollient to web 10 as printing, extruding, or bathing. Preferred are low contact pressure methods and especially preferred are treatment methods in which there is no contact pressure, so as to preserve the low density character of wiping zone 18. In the preferred embodiment the lipophilic cleansing emollient was sprayed onto web 10.

The quantity of lipophilic cleansing emollient applied to web 10 must be sufficient to coat the area being wiped with a thin film of lipophilic cleansing emollient.

The quantitiy of lipophilic cleansing emollient is easily given with reference to the weight of web 10 and may vary between about 10 and about 10 and about 150 percent of the weight of web 10. More preferably the weight of the lipophilic cleansing emollient added to web 10 will be from about 20 to about 100 percent of the weight of web 10. Most preferably, web 10 is treated with from about 50 to about 70 percent by weight of web 10 of lipophilic cleansing emollient.

It has now been discovered that there is a correlation between the cleaning effectiveness of web 10 when treated with a lipophilic cleansing emollient and the porosity of the wiping zone 18 as indicated by the average void index (at least 68). By manufacturing webs 10 such that the average void index is high (i.e., an average void index of at least 68 under a pressure of 1 psi [7 kilopascals]) the treating of web 10 with a lipophilic cleansing emollient results in an unexpected improvement in cleaning effectiveness and importantly the improved cleansing is achieved without a concomitant increase in the pressure applied to the area being wiped. Web 10 must, however, have a high average void index (at least 68) under the normal pressure encountered during the anal wiping process which is about 1 psi (7 kilopascals).

Listed in Table I are the results of cleaning tests conducted on four webs 10 in accordance with the procedure hereinbefore described. The first two webs 10, A and B, have low average void indices (33.7 and 62.6 respectively) and are thus high density products while the remaining two webs 10, C and D, have high average void indices (77.1 and 82.4 respectively) and are therefore low density products. For each web 10, the minimum void index is also listed. The minimum void index is important because it indicates the presence or absence of a fecal impermeable layer within wiping zone 18 which may prevent web 10 from cleaning effectively.

As can be clearly seen from Table I, webs 10 having relatively low average void indices (A and B) do not exhibit any substantial improvement in cleansing effectiveness when treated with a lipophilic cleansing emollient. The maximum improvement in cleaning effectiveness when a dry web 10 is treated with a lipophilic cleansing emollient is only about 11 percent. It should be noted, however, that the addition of lipophilic cleansing emollients can have the opposite effect from that which is desired and can actually degrade the cleaning ability of webs 10 having low average void indices by as much as 6.6 percent (as for web A and treatment 1). In contrast, webs 10 having a high average void index (C and D) exhibit an improvement in cleaning effectiveness ranging from about 18 to about 37 percent over the corresponding untreated webs 10.

TABLE I

| (Col.1) Web | (Col.2) Avg. Void Index/ Min. Void Index | (Col.3) Weight of Fecal Matter Remaining on Test Skin After 8 Wipes With an Untreated Web (mg) | (Col.4) Weight of Fecal Matter Remaining on Test Skin After 8 Wipes With a Treated (2) Web (mg) | (Col.5) % Improvement in Cleaning of Treated (2) Web Over the Corresponding Untreated Web | (Col.6) Weight of Fecal Matter Remaining on Test Skin After 8 Wipes With a Treated (3) Web (mg) | (Col.7) % Improvement in Cleaning of Treated (3) Web Over the Corresponding Untreated Web | (Col.8) Weight of Fecal Matter Remaining on Test Skin After 8 Wipes With a Treated (4) Web (mg) | (Col.9) % Improvement in Cleaning of Treated (4) Web Over the Corresponding Untreated Web | (Col.10) Weight of Fecal Matter Remaining on Test Skin After 8 Wipes With a Treated (5) Web (mg) | (Col.11) % Improvement in Cleaning of Treated (5) Web Over the Corresponding Untreated Web |
|---|---|---|---|---|---|---|---|---|---|---|
| A | 33.7/21.8 | 10.6 | 11.3 | −6.6 | 9.4 | 11.3 | 10.0 | 5.7 | 10.0 | 5.7 |
| B | 62.6/57.0 | 10.5 | 10.7 | −1.9 | 9.4 | 10.5 | 9.4 | 10.5 | 10.0 | 4.8 |
| C | 77.1/73.2 | 8.2 | 5.2 | 36.6 | 6.6 | 19.5 | 5.9 | 28.0 | 6.4 | 22.0 |
| D | 82.4/77.4 | 7.6 | 6.1 | 19.7 | 5.4 | 28.9 | 4.9 | 35.5 | 6.2 | 18.4 |

NOTES
(1)All lipophilic cleansing emollients are added in a quantity equal to 70% of the weight of the web.
(2)Lipophilic cleansing emollient is petrolatum.
(3)Lipophilic cleansing emollient is a mixture of: 50% Isopropyl palmitate; 25% cetyl alcohol; 20% petrolatum; and 5% Brij 72.
(4)Lipophilic cleansing emollient is a mixture of: 70% Isoprpoyl palmitate; 25% cetyl alcohol; and 5% Brij 72.
(5)Lipophilic cleansing emollient is a mixture of: 65% petrolatum; 30% Mineral Oil; and 5% Brij 72.

While not wishing to be bound by any one theory describing the operation of the present invention, it is believed that the lipophilic cleansing emollient improves the cleaning effectiveness of web 10 in the manner now to be described. When the anal area is wiped with a web 10 which has been treated with a lipophilic cleansing emollient, the lipophilic cleansing emollient is released and transferred from web 10 thereby coating the fecal matter and the anal skin with a thin film. Since the lipophilic cleansing emollient is essentially nonhygroscopic, the fecal matter is neither dehydrated, appreciably, nor reconstituted. In addition, the lipophilic cleansing emollient spreads on the skin and is able to migrate between the fecal matter and the anal skin thereby reducing the soil-skin adhesive forces making the continued mechanical removal of the soil during wiping easier. During the wiping process the fecal matter penetrates web 10 and becomes entrapped in the surface and subsurface voids. A web 10 having surface voids is particularly effective when treated with a lipophilic cleansing emollient because such surfaces will not slide over coated fecal matter but will rather dig into the soil and remove it by mechanical entrapment.

In order to contribute to a better understanding of this invention and not by way of limitation, the following examples are provided.

EXAMPLE I

A single ply web manufactured using a layering process and having two layers was treated with a lipophilic cleansing emollient consisting of, by weight, 65 percent petrolatum, 30 percent mineral oil and 5 percent nonionic surfactant. The nonionic surfactant used was polyoxyethylene (2) stearyl ether marketed under the tradename Brij 72 by Atlas Chemical Division ICI America Inc. of New Castle, Delaware.

The lipophilic cleansing emollient was sprayed on the web in a quantity equalling 70 percent of the weight of the web. The web was manufactured in accordance with the description hereinbefore given. The treated web felt soft and pleasing to the touch and exhibited efficient and effective cleaning characteristics when used for anal cleaning. The improved cleaning results achieved with this treated web are shown in Table I as web D under Columns 10 and 11. Thus, web D treated with the lipophilic cleansing emollient described in Example I (see Table I, footnote 5) cleans 18.4 percent better than untreated web D. By comparison low average void index webs A and B when treated with the same lipophilic cleansing emollient exhibit only a 5.7 and 4.8 percent cleaning improvement, respectively, when compared to the corresponding untreated webs A and B.

EXAMPLE II

The web described in Example I was treated with a lipophilic cleansing emollient consisting of, by weight, 50 percent isopropyl palmitate, 25 percent cetyl alcohol, 20 percent petrolatum, and 5 percent noionic surfactant. The nonionic surfactant used is the same as was used in Example I. The lipophilic cleansing emollient was sprayed on the web in a quantity equal to 70 percent of the weight of the web. The improved cleaning results achieved with this treated web are shown in Table I as web D under Columns 6 and 7. Thus, web D treated with the lipophilic cleansing emollient described in Example II (see Table I, footnote 3) cleans 28.9 percent better than untreated web D. By comparison low average void index webs A and B when treated with the same lipophilic cleansing emollient exhibit only a 11.3 and 10.5 percent cleaning improvement, respectively when compared to the corresponding untreated webs A and B.

It will be understood by those skilled in the art that the invention has been described with reference to an exemplary embodiment and that variations and modifications can be effected in the described embodiment without departing from the scope and spirit of the invention.

For example, in addition to being used for anal cleaning, the web 10 may be used for cleaning the urogenital region or for removing soil and makeup from the facial regions. Further, web 10 may be manufactured from foams such as polyurethane or from cellulosic sponges.

In order to more fully appreciate the spirit and scope of the invention, reference should be made to the appended claims.

What is claimed and desired to be secured by Letters Patent of the United States is:

1. A soft, pliant, skin cleansing product comprising a web having a wiping surface and a low density wiping zone; said wiping surface being one boundary of said wiping zone; said wiping zone being soil permeable and having surface depressions which contribute to the contours of said wiping surface and having subsurface voids below said wiping surface, said wiping zone having an average void index as determined under a pressure of 1 pound per square inch of at least 68 and a minimum void index of at least 10; said wiping zone being treated with from about 10 percent to about 150 percent by weight of said web of a lipophilic cleansing emollient.

2. A soft pliant, skin cleansing product comprising a web having a wiping surface and a low density wiping zone; said wiping surface being one boundary of said wiping zone; said wiping zone being soil permeable and having surface depressions which contribute to the contours of said wiping surface and having subsurface voids below said wiping surface, said wiping zone having an average void index as determined under a pressure of 1 pound per square inch of at least 70 and a minimum void index of at least 10; said wiping zone being treated with from 20 percent to about 100 percent by weight of said web of a lipophilic cleansing emollient.

3. A soft, pliant, skin cleansing product comprising a web having a wiping surface and a low density wiping zone; said wiping surface being one boundary of said wiping zone; said wiping zone being soil permeable and having surface depressions which contribute to the contours of said wiping surface and having sursurface voids below said wiping surface, said wiping zone having an average void index of at least 75 and a minimum void index as determined under a pressure of 1 pound per square inch of at least 10; said wiping zone being treated with from about 50 percent to about 70 percent by weight of said web of a lipophilic cleansing emollient.

4. The product of claim 1 wherein said web is fibrous.

5. The product of claim 1 wherein said web is paper.

6. The product of claim 5 wherein said web is manufactured by a layering process.

7. The product to claim 6 wherein said paper web comprises a single ply having two layers.

8. The product of claim 1 wherein said lipophilic cleansing emollient is nonhygroscopic and has a viscosity no greater than 5,000 cps at a shear rate of 400 seconds $^{-1}$ at 25° C.

9. The product of claim 8 wherein said lipophilic cleansing emollient comprises a mixture of: petrolatum, mineral oil, and a non-ionic surfactant.

10. The product of claim 8 wherein said lipophilic cleansing emollient comprises a mixture of: isopropyl palmitate, cetyl alcohol, non-ionic surfactant and petrolatum.

11. The product of claim 1 wherein said web is a multi-ply structure.

12. The product of claim 1 wherein said web comprises a single ply of a unitary paper.

13. A soft, pliant toilet tissue product comprising a web having a wiping surface and a low density wiping zone; said wiping surface being one boundary of said wiping zone; said wiping zone being soil permeable and having surface depressions which contribute to the contours of said wiping surface and having subsurface voids below said wiping surface, said wiping zone having an average void index of at least 75 and a minimum void index as determined under a pressure of 1 pound per square inch of at least 10; said wiping zone being treated with from about 50 percent to about 70 percent by weight of said web of a lipophilic cleansing emollient.

14. The toilet tissue product of claim 13 wherein said lipophilic cleansing emollient comprises a mixture of: isopropyl palmitate, cetyl alcohol, non-ionic surfactant and petrolatum.

15. The toilet tissue product of claim 14 wherein said web is manufactured by a layering process and comprises two layers.

* * * * *

UNITED STATES PATENT AND TRADEMARK OFFICE
CERTIFICATE OF CORRECTION

PATENT NO. : 4,112,167
DATED : September 5, 1978
INVENTOR(S) : Timothy W. Dake et al It is certified that error appears in the above-identified patent and that said Letters Patent are hereby corrected as shown below:

Column 3, line 50, "lower" should read --low--.

Column 4, line 35, "Multiply" should read --Multi-ply--.

Column 11, line 3, "and about 10" should be omitted.

Signed and Sealed this

Fifth Day of June 1979

[SEAL]

Attest:

RUTH C. MASON
*Attesting Officer*

DONALD W. BANNER
*Commissioner of Patents and Trademarks*